(12) United States Patent  
Dietrich et al.

(10) Patent No.: US 11,696,963 B2
(45) Date of Patent: Jul. 11, 2023

(54) POWDER STERILIZATION METHOD AND DEVICE (71) Applicant: FYDEC HOLDING SA, Ecublens (CH)

(72) Inventors: Yves Dietrich, Ecublens (CH); Frederic Dietrich, Morrens (CH)

(73) Assignee: FYDEC HOLDING SA, Ecublens (CH)

( * ) Notice: Subject to any disclaimer, the term of this patent is extended or adjusted under 35 U.S.C. 154(b) by 216 days.

(21) Appl. No.: 16/756,324

(22) PCT Filed: Oct. 16, 2017

(86) PCT No.: PCT/EP2017/076355
§ 371 (c)(1),
(2) Date: Apr. 15, 2020

(87) PCT Pub. No.: WO2019/076434
PCT Pub. Date: Apr. 25, 2019

(65) Prior Publication Data
US 2020/0316235 A1 Oct. 8, 2020

(51) Int. Cl.
*A61L 2/07* (2006.01)
*A23L 3/18* (2006.01)
(Continued)

(52) U.S. Cl.
CPC ............... *A61L 2/07* (2013.01); *A23C 3/037* (2013.01); *A23L 3/185* (2013.01); *A23L 3/50* (2013.01);
(Continued)

(58) Field of Classification Search
CPC .... A61L 2/07; A61L 2/0023; A61L 2202/121; A61L 2202/122; A61L 2202/15;
(Continued)

(56) References Cited

U.S. PATENT DOCUMENTS 2,303,422 A  12/1942 Ball
4,597,945 A  7/1986 Sugisawa et al.
(Continued)

FOREIGN PATENT DOCUMENTS

CN    107197934 A   9/2017
DE    19818224 B4   6/2005
(Continued)

OTHER PUBLICATIONS

International search report for patent application No. PCT/EP2017/076355 dated Jun. 5, 2018.

*Primary Examiner* — Sean E Conley
*Assistant Examiner* — Brendan A Hensel
(74) *Attorney, Agent, or Firm* — Bachman & LaPointe, P.C.

(57) ABSTRACT

A powder sterilization method for sterilizing powder, in particular an active pharmaceutical ingredient in powder form or food in powder form, using fluid vapor, in particular steam. According to the invention, the fluid vapor is applied to the powder in an evacuated treatment chamber (3), in particular it is applied to the powder during its free fall along a drop section (7), in particular in countercurrent.

12 Claims, 5 Drawing Sheets (51) Int. Cl.
  *A23L 3/50* (2006.01)
  *A61L 2/00* (2006.01)
  *A23C 3/037* (2006.01)
  *B65B 1/16* (2006.01)
  *B65B 55/14* (2006.01)
  *B65B 55/18* (2006.01)
(52) U.S. Cl.
  CPC .............. *A61L 2/0023* (2013.01); *B65B 1/16* (2013.01); *B65B 55/14* (2013.01); *B65B 55/18* (2013.01); *A61L 2202/121* (2013.01); *A61L 2202/122* (2013.01); *A61L 2202/15* (2013.01)
(58) Field of Classification Search
  CPC ..... A61L 2202/12; A23C 3/037; A23L 3/185; A23L 3/50; A23L 3/245; B65B 1/16; B65B 55/14; B65B 55/18
  See application file for complete search history.

(56) References Cited

U.S. PATENT DOCUMENTS

| | | |
|---|---|---|
| 2005/0037119 A1 | 2/2005 | Taniguchi |
| 2010/0266467 A1* | 10/2010 | Laumer .................. A61L 2/208 |
| | | 422/291 |
| 2013/0320035 A1 | 12/2013 | Dietrich, Jr. |
| 2016/0242454 A1* | 8/2016 | Waeny ................ A23B 7/0053 |

FOREIGN PATENT DOCUMENTS

| | | | |
|---|---|---|---|
| DE | 102010054649 B3 | 4/2012 | |
| DK | 0 803 203 | * 10/1997 | .............. A23L 3/16 |
| EP | 0803203 A2 | 10/1997 | |
| JP | 2005058916 A | 3/2005 | |
| JP | 2013202024 A | 10/2013 | |
| WO | 2009003546 A1 | 1/2009 | |

* cited by examiner

POWDER STERILIZATION METHOD AND DEVICE

BACKGROUND OF THE INVENTION

The invention relates to a powder sterilization method for sterilizing powder, in particular an active pharmaceutical ingredient powder or a food powder, such as milk powder, using fluid vapor, in particular steam, the fluid vapor being applied to the powder in an evacuated treatment chamber, i.e., a treatment chamber to which negative pressure is applied or which is at a negative pressure level.

Furthermore, the invention relates to a powder sterilization device which is realized for performing a powder sterilization method according to the invention, the device having an, in particular elongated, more preferably tubular, vessel (reactor) limiting the, preferably also elongated, treatment chamber and the device having evacuation means assigned to said vessel, in particular comprising a vacuum pump, for evacuating the treatment chamber, i.e., for applying negative pressure to the treatment chamber. Furthermore, the powder sterilization device comprises fluid vapor application means for applying the fluid vapor to the powder in the evacuated treatment chamber. The fluid vapor application means preferably comprise a vapor generator and at least one vapor line for supplying the fluid vapor, in particular the steam, into the treatment chamber of the vessel via at least one outlet opening, particularly preferably via at least one outlet nozzle.

Sterilization, i.e., the reduction of the number of germs per quantity of material, is usually a corresponding treatment of surfaces. When sterilizing surfaces, such as natural surfaces of parts of plants or pieces of meat or artificial surfaces, it is essential, in addition to a high level of sterilization efficiency, to preserve the initial state of the materials which are limited by the surfaces as much as possible. In practice, the sterilization of powder, i.e., of material particle bulks, is particularly difficult.

Different methods are known for sterilization; said methods can be divided into chemical, physical and thermal methods. For the germ reduction of spice plants and medicinal plants, the use of chemical methods, such as an ethylene oxide and ozone treatment, is known, although there are health concerns regarding the former. The use of physical methods is also known, in particular irradiation using ionizing radiation; however, the use of ionizing radiation for sterilizing food is forbidden today. Furthermore, high-pressure sterilization methods at very high pressures of up to 7000 bar are known.

According to the disclosure of DE 198 18 224 B4, the GB book "Engineering and Food", Vol. 2, Elsevier London 1984, page 595, describes a thermal sterilization method for powder using superheated vapor. The disadvantage of the known method is that it is not possible to transmit a large amount of energy to the material in a short period of time by condensing the vapor.

A method which is improved in that regard but cannot be applied to powders is described in DE 198 18 224 B4. At the heart of the known method, saturated vapor is applied to the material to be treated and the condensate formed on the material to be treated is subsequently evaporated by reducing the pressure in a treatment chamber so that the substances are dried. With respect to powders, the known method would result in clumping.

WO 2009/003546 A1 also describes a method for sterilizing surfaces of pieces of food, saturated vapor being applied to the pieces of food while applying a stirring force, said saturated vapor condensing on the pieces of food product, the condensate being evaporated again by reducing the pressure in a corresponding manner. The known method cannot be used for powders due to its tendency to cause clumping.

DE 10 2010 054 649 B3 also describes a powder metering method and a powder metering device. U.S. Pat. No. 2,303,422 A describes a method for filling foods. US 2005/0037119 A1 discloses the dissolution of a raw material, fusion of a raw material or treatment for enhancing the fluidity of a raw material by applying fluid vapor.

EP 0 803 203 A describes a method in which the powder is conveyed as a debris to the upper end of the drop section and subsequently passes through the drop section before it is transported back to the upper end of the drop section by means of an elevator arrangement. Prior to the beginning of the powder treatment, a negative pressure is generated, so that dry atmosphere can be removed entirely. After that and also prior to the powder treatment, a positive pressure atmosphere which is moist or which comprises fluid vapor is generated, the powder treatment being realized in said atmosphere.

The dissertation "Quality preservation of functional food powder by short-time vacuum-steam-vacuum decontamination treatment" by Josef T. Hörmansperger describes a drop tower for decontaminating powder in which a negative pressure or vacuum is applied or generated before the powder passes through a drop section in which fluid vapor is applied to the powder. In a subsequent step, a vacuum or negative pressure is applied again to the powder which is collected in the bottom area of the drop tower.

Starting from the aforementioned state of the art, the object of the invention is to indicate an improved method for sterilizing powder by means of which the powder can be sterilized as gently as possible. Furthermore, the object is to indicate an accordingly improved powder sterilization device for performing a powder sterilization method according to the invention.

Concerning the powder sterilization method, said object is attained by the features disclosed herein.

Steam is particularly preferably used as the fluid vapor, although fluids other than steam can also be used.

Concerning the powder sterilization device, the object is attained by the features disclosed herein.

The present disclosure focuses on the explanation of the method according to the invention. Even if it is not explicitly mentioned, the device comprises corresponding functional means for performing corresponding method steps which are in each case seen as disclosed features relating to the device and are thus also claimable therefor. With respect to the description of a preferred heating of the treatment chamber, for example, the device comprises corresponding heating means.

Advantageous embodiments of the invention are disclosed herein and in the dependent claims. All combinations of at least two features disclosed in the description, the claims and/or the figures constitute part of the scope of the invention.

In order to avoid repetitions, disclosed features relating to the device are also seen as relating to the method and are thus also claimable therefor. In the same manner, disclosed features relating to the method are also seen as relating to the device and are thus also claimable therefor.

The invention is based on the realization that the application of high temperatures has to be as short as possible for a gentle sterilization of powder; this can be realized by applying fluid vapor, in particular saturated vapor, in order to avoid or minimize thiamin losses, lipid oxidations or Maillard reactions depending on the composition of powder.

In order to allow for the use of a fluid vapor sterilization for powder and to avoid clumping, according to the invention, fluid vapor is not applied to the powder while the powder is in the form of a heap or during mechanical mixing) but during a free fall, i.e., when the powder is trickling or falling along a drop section provided according to the invention, which extends along the vertical. Furthermore, the invention has realized that the effectiveness of the sterilization can be significantly improved if the vapor application takes place during the free fall in the negative pressure, i.e., below the normal pressure. In other words, the powder, in particular in the form of a powder cloud, trickles along the drop section into an evacuated treatment chamber where the fluid vapor application is then realized. The evacuation of the treatment chamber ensures that an air barrier or air cushion which prevents the direct contact of the fluid vapor and the powder, i.e., the material particles, does not exist or is at least reduced or cannot be realized, a direct contact of the fluid vapor and the powder or a close contact between the fluid vapor and the powder thus being ensured. The fluid vapor is therefore not diverted around the powder particles, but it directly contacts said powder particles.

So according to the sterilization method according to the invention and the powder sterilization device according to the invention, the fluid vapor is applied, in particular in countercurrent, to the powder in an evacuated treatment chamber, i.e., a treatment chamber to which a pressure below normal pressure is applied or which is at a pressure below normal, during a free fall of the powder as the powder is trickling along a drop section. For realizing the drop section, the device comprises a treatment chamber which has or includes the drop section and which is elongated, in particular along a vertical, and which can be evacuated by means of corresponding evacuation means, in particular a vacuum pump, and in which fluid vapor can be applied to powder during the free fall of the powder along the drop section, for which purpose at least one fluid vapor outlet opening is preferably disposed along and/or below the drop section, in particular in such a manner that fluid vapor is blown out, preferably diagonally, upwards in order to generate a countercurrent to the powder which trickles downwards.

With respect to the specific embodiment of the powder, different possibilities are available. The powder can be a food powder, in particular milk powder, which generally tends to clump. The powder can also be an active pharmaceutical ingredient, etc. An average particle size of the powder particles, in particular an average particle diameter $X_{50,3}$ of the powder particles, is preferably selected from a range between 0.1 µm and 200 µm, particularly preferably between 1 µm and 100 µm.

In a particularly preferred embodiment of the method according to the invention or of the device according to the invention, the fluid vapor, in particular saturated vapor, condenses on a powder surface, i.e., the surface of the powder particles, which results in an optimized heat transfer, allowing the duration of the application of high temperature to the powder particles to be reduced to a very short period of time, the powder being dried (again) before being discharged from the treatment chamber in order to avoid clumping of the powder in the case of condensation on the surface, the drying being realized by evaporating condensate from the powder surface, which can be achieved by a corresponding application or control of the temperature and, in particular, of the negative pressure. It is particularly useful to use the drop section for the drying process in such a manner that a fluid vapor application section of the drop section is followed by a drying section of the drop section in which the condensate is at least partially, preferably largely, particularly preferably evaporated from the powder surface, in particular by applying a corresponding negative pressure to the drop section or to the treatment chamber including the drop section. As a result, sterilized and dried powder arrives at the lower end of the drop section and can be or is discharged from the treatment chamber, in particular in the form of a heap which is formed.

In a particularly preferred embodiment of the method according to the invention and of the device according to the invention, the powder to be sterilized is supplied to the treatment chamber which is at a first negative pressure level, preferably between 0.1 mbar (or less) and 300 mbar absolute, particularly preferably between 0.1 mbar and 100 mbar absolute (a pressure of more than 0.1 mbar absolute, for example of 0.5 mbar or 0.1 bar absolute, being realizable or conceivable as the lower limit of the first negative pressure level, in principle) and the fluid vapor is applied to said powder during the free fall along the drop section, the pressure level in the treatment chamber rising to an increased second pressure level (either a negative pressure level, a normal pressure level or a positive pressure level) compared to the first negative pressure level, in particular by supplying or introducing the fluid vapor), preferably at a treatment chamber pressure of more than 0.5 bar absolute, preferably to a pressure from a range between 0.7 bar and 4 bar absolute, in particular between 1 bar and 3 bar absolute, and that the pressure level is reduced to dry the powder, in particular during the free fall of the powder along the drop section, in particular to a (third) negative pressure level, preferably from a range between 0.1 mbar (or less) and 600 mbar absolute, particularly preferably between 0.1 mbar and 300 mbar absolute, before the powder is discharged from the treatment chamber. According to the invention, the evacuation means are operated in a permanent, i.e., continuous manner to provide the negative pressure (in particular the first negative pressure level and the third negative pressure level) in the treatment chamber, a suction pressure thus being permanently applied and the application of fluid vapor causing the pressure to rise during the free fall after the powder has been supplied; as already mentioned, the evacuation means, in particular a vacuum pump, continue to apply suction to the treatment chamber during said fluid vapor application. In a particularly preferred embodiment, the third negative pressure level to which the absolute pressure in the treatment chamber (reactor chamber) is reduced during the free fall of the powder along the drop section to dry the powder corresponds to the first (absolute) negative pressure level. If the drop time or drop section is insufficient to reduce the pressure to the first negative pressure level during the free fall of the powder particles, the third negative pressure level can be higher than the first negative pressure level, the treatment pressure level being preferably reduced (again) to the first negative pressure level before a new powder portion to be sterilized and to be dried is supplied. A third negative pressure level of at least 600 mbar or less is preferably reached during the free fall.

The aforementioned process is preferably repeated for each new powder portion, the short treatment times resulting in a quasi-continuous sterilization and drying.

The method is particularly preferably realized in such a manner that fluid vapor is not permanently fed into the drop section, but only during a period of time of the powder treatment. The feeding of fluid vapor is particularly preferably interrupted or does not take place while powder to be sterilized is being supplied into the vessel and/or during the drying phase, in particular while the powder is falling through the drying section.

In order to reduce the time for realizing a negative pressure level, powder to be sterilized is supplied to the already evacuated treatment chamber (i.e., the treatment chamber is at an, in particular the first, negative pressure level) via an inlet negative pressure lock, in particular an impeller lock, and after the free fall along the drop section and after the simultaneous application of fluid vapor, the powder (which is thereby sterilized and preferably already dried) is discharged from the treatment chamber via an outlet negative pressure lock, in particular an impeller lock.

Powder to be sterilized is particularly preferably supplied in portions to and/or discharged in portions from the treatment chamber, which can be realized in a particularly simple manner by means of cells of an impeller lock. A supply in portions or in batches allows for an approach which is clocked in a particularly simple manner and within the scope of which each powder portion falls along the drop section separately, fluid vapor is applied to each powder portion for a limited period of time and each powder portion is preferably dried during the free fall. It is possible in principle to supply powder be to sterilized to the treatment chamber via the aforementioned inlet negative pressure lock exclusively during or exclusively after the discharging of sterilized powder, in particular via the aforementioned outlet negative pressure lock. However, an overlapping of said processes is also possible, i.e., in such a manner that powder to be sterilized is supplied to the treatment chamber or can be supplied within the scope of the device during and after the discharge process for discharging sterilized powder.

In a particularly preferred embodiment of the invention, a volumetric powder metering device is provided or is disposed upstream of the treatment chamber as a negative pressure lock for supplying powder to be sterilized into the treatment chamber, said volumetric powder metering device being realizable as described in EP 2 652 541 B1, for example. Such a powder metering device is preferably characterized by a metering chamber which is or can be connected to a negative pressure line for applying negative pressure to the metering chamber in order to suck powder to be sterilized from a powder reservoir and to fill the metering chamber with powder to be sterilized. The metering chamber volume (powder volume to be sterilized) can then be discharged towards the treatment chamber, preferably directly into the treatment chamber, in particular by connecting it to a compressed gas line and/or via an adjustable discharge plunger, the metering chamber being preferably closed on the outlet side by suitable, preferably negative pressure-sealed, closing means, for example by means of a flap or a slide, during the filling process of the metering chamber by aspirating powder to be sterilized, the metering chamber thereby being preferably decoupled from the treatment chamber with respect to the pressure. After opening the closing means, the (metered) powder can move from the metering chamber into the treatment chamber and fall freely. By providing a powder metering device based on negative pressure as a negative pressure lock, pressure or negative-pressure losses, which are difficult to avoid or can be avoided with great effort when using an impeller lock, can be avoided in a reliable manner. Furthermore, a precise volumetric metering of powder portions to be sterilized one after the other is possible. The powder metering device is preferably characterized by a negative pressure connection and a compressed gas connection, via which negative pressure and positive pressure can be applied in an alternating manner to the metering chamber in order to fill and to discharge the negative pressure chamber. The metering chamber volume is preferably adjustable, in particular by axial displacement of a facultative plunger which can be or preferably is disposed so as to be displaceable into the treatment chamber in addition or as an alternative to a pressure application for discharging the powder to be sterilized.

In a particularly preferred embodiment, fluid vapor enters the treatment chamber or can be supplied to the treatment chamber at an increased pressure, in particular from a range between 1.1 bar and 6 bar (absolute), more preferably between 1.1 bar and 4 bar (absolute), compared to the pressure level in the treatment chamber at the beginning of the fluid vapor application, in particular by means of a corresponding realization of the fluid vapor application means, in particular of a vapor generator.

As already mentioned, it is particularly advantageous if fluid vapor and powder move in countercurrent, for which it is necessary that the fluid vapor can jet upwards, i.e., in the vertical direction, with at least one directional component. It is also conceivable in principal to feed the fluid vapor in an exactly vertical manner—in a particularly preferred embodiment, however, an angle between a main jetting direction of the fluid vapor from at least one corresponding outlet opening, in particular an outlet nozzle, and the vertical is between 1° and 60°, particularly preferably between 5° and 45°, more preferably between 10° and 30°. Such an implementation of the method or realization of the device can be realized in a particularly suitable manner by providing a ring outlet assembly, in particular a ring nozzle assembly.

It is particularly useful if the fluid vapor enters or can be fed into the treatment chamber at several points along the drop section which are spaced apart in the vertical direction and/or at several points which are spaced apart in the circumferential direction (around a drop axis), which is achieved by accordingly providing different outlet openings, in particular outlet nozzles.

A particularly preferred embodiment provides several ring nozzle assemblies disposed above one another along the vertical and each having a plurality of outlet nozzles for fluid vapor spaced apart in the circumferential direction. According to a simple embodiment, a single ring nozzle assembly can be disposed in the area of the drop section or below said section, but in any event in such a manner that the fluid vapor can be applied to the powder during the free fall.

It is particularly useful if the fluid vapor which is fed into the treatment chamber is saturated or, alternatively, in particular slightly, superheated (when the vapor enters the treatment chamber), in particular by a corresponding realization and/or a corresponding operation of the fluid vapor application means, in particular of a fluid vapor generator, said fluid vapor particularly preferably having a temperature from a range between 101° C. and 200° C. or higher, particularly preferably between 110° C. and 160° C., when it enters the treatment chamber.

As already stated, the fed fluid vapor can be saturated vapor (when the vapor enters)—however, a preferred embodiment provides that the vapor is superheated when the vapor enters in order to reduce the amount of condensate—the vapor will become saturated in the negative pressure atmosphere in any case. The vapor parameters (pressure, temperature, moisture content) are preferably selected in such a manner that a condensation of the vapor in the at least one vapor line between a vapor generator and the outlet openings, in particular nozzles, is prevented, which means in particular that no condensate can be injected into the treatment chamber. Since the vapor loses or emits a high amount of energy due to the expansion in the negative pressure when the vapor is injected into the treatment chamber, but a high amount of energy is preferably available for the inactivation or destruction of germs or microorganisms, superheating of the vapor (upon entry of the vapor) is expedient or preferred.

In order to avoid vapor condensation at the vessel wall and to accelerate the preferred, facultative drying process, it has been found advantageous for the treatment chamber to be heated to a temperature from a range between 150° C. and 400° C., preferably between 180° C. and 250° C., during the sterilization process. For this purpose, a wall heating device can be used, for example, in particular an oil or steam heating device, in order to be able to easily set or maintain temperatures above 100° C. In terms of output, the heating device is preferably dimensioned in such a manner that the temperature of the treatment chamber, as a first approximation, corresponds to the flow temperature of the heating device.

In general, the supplied powder can fall along the drop section directly from a supply position without further action, in particular after passing the inlet negative pressure lock. In order to improve powder cloud formation, i.e., to disperse the powder in a better, in particular more uniform, manner and to give more time for the trickling process, if required, powder particles thus falling one after the other along the drop section in a loosened manner and distributed over a period of time in order to ensure that fluid vapor comes into contact with or is applied to a majority, in particular all of the particles, corresponding functional means are provided in an embodiment of the invention and are either integrated into the supply system or preferably disposed downstream of said supply system. The improvement of the powder cloud formation by corresponding functional means is particularly preferably realized as a separate step after supplying the powder into the treatment chamber. The functional means are realized so as to improve powder cloud formation, in particular by separating or swirling and/or loosening the supplied powder, in particular a supplied powder portion. For example, mechanical dispersing and/or loosening means, in particular comprising vibration means, can be provided by means of which a sieve, for example, can be caused to vibrate in order to loosen and to disperse the powder, the powder having to pass through said vibrating element, in particular the sieve, upstream of or in the upper area of the drop section. It is also conceivable to use flow-mechanical dispersing and/or loosening means, such as gas nozzles, which loosen or swirl the supplied powder, in particular a powder portion.

The fluid vapor is/can be particularly preferably applied to the powder during a drop time of no more than between 0.05 s and 2 s, in particular between 0.1 s and 1.5 s, more preferably between 0.1 s and 0.5 s.

The powder, in particular a food powder, is particularly preferably dried by the drying process to a maximum residual moisture content of 15 wt.-%, particularly preferably 5 wt.-%, more preferably 4 wt.-%. It has proven advantageous for pharmaceutical applications if the, in particular pharmaceutical, powder, particularly preferably an active pharmaceutical ingredient, is dried to a maximum residual moisture content from a range between 0 wt.-% and 5 wt.-%, preferably between 0.01 wt.-% and 5 wt.-%, more preferably between 0.1 wt.-% and 3 wt.-%, particularly preferably between 0.1 wt.-% and 1 wt.-%.

The axial extension, i.e., the length of the drop section along the vertical, is preferably selected from a range between 2 m and 30 m, in particular between 4 m and 15 m.

The inner diameter of the treatment chamber is preferably selected from a range between 50 mm and 2000 mm, particularly preferably between 80 mm and 1000 mm.

The treatment chamber can be and is preferably realized so as to be empty or free on the inside, i.e., in its radial center, in particular if it has a hollow-cylindrical contour, particularly preferably a hollow-circular-cylindrical contour. Alternatively, the treatment chamber can be and is preferably realized as a ring chamber around an, in particular filled, center (center section) in order to realize high mass flow rates, in which case the vapor is introduced not only from one direction, in particular not only from the radial outside, but also from the central or inner area. In other words, an embodiment of the invention provides the realization of a treatment chamber having an annular, in particular circular shape in a cross-sectional view and the disposition of vapor outlet openings, in particular nozzles, particularly preferably ring nozzles, both in the area of an outer wall of the vessel (on its inside) limiting the treatment chamber on the radial outside and in the area of a centric or inner vessel wall (on its outside) limiting the treatment chamber on the radial inside. Fluid vapor can thus be applied in a particularly uniform manner to large chamber volumes in order to ensure good mixing with the powder or a powder portion.

A ratio from a range between 20 and 150, particularly preferably between 40 and 100, between a length of the drop section and an inner diameter has proven to be particularly suitable, the inner diameter being measured at two diametrically opposed points of an outer wall of the vessel limiting the treatment chamber on the radial outside, the treatment chamber being limited on the inside by an, in particular circular cylindrical, center section, which is particularly preferably continuous in the axial direction or, alternatively, provided in sections in the axial direction, in the case of larger inner diameters, in particular of more than 500 mm, the supplying of vapor into the treatment chamber, which has an annular contour in that case, particularly preferably taking place from the radial outside and from the radial inside.

In a particularly preferred embodiment of the method according to the invention and of the device according to the invention, the device has a packaging device for the, in particular sterile, packaging of sterilized powder into a final packaging, in particular pouch packaging. The packaging device is particularly preferably disposed in such a manner that it is disposed downstream of the treatment chamber, in particular below the treatment chamber along the vertical, and/or in such a manner that sterilized powder can be transferred into final packaging by gravity, preferably in a falling or sliding manner.

If, preferably, several treatment chambers or vessels are provided, their outlets preferably lead to a common reservoir or to a common packaging device, allowing powder which is sterilized and preferably dried in at least two different treatment chambers to be supplied to a common packaging device, in particular by gravity, allowing powder from at least two treatment chambers to be supplied to a common packaging device and, in particular, to common final packaging.

Furthermore, the invention relates to a system comprising at least two devices according to the invention, wherein sterilized powder from said devices can be brought together towards a common packaging device and/or towards a common reservoir. The system is based on a modular concept, because, from a technical point of view, the production of higher quantities of powder to be sterilized is surprisingly simpler to realize by providing a plurality of, preferably identical, devices that are smaller compared to a single, larger device. Particularly advantageously, powder mass flows from two devices or two treatment chambers are merged and thereby preferably mixed. Preferably, powder masses from at least two treatment chambers are merged and are supplied to a common reservoir and are packed together, in particular by means of a common packaging device, said packaging device being particularly preferably supplied by means of gravity, the packaging device thus being disposed below the devices along the vertical.

BRIEF DESCRIPTION OF THE DRAWINGS

Further advantages, features and details of the invention can be derived from the following description of preferred exemplary embodiments and from the drawings.

In the following.

DETAILED DESCRIPTION

Figure 1:
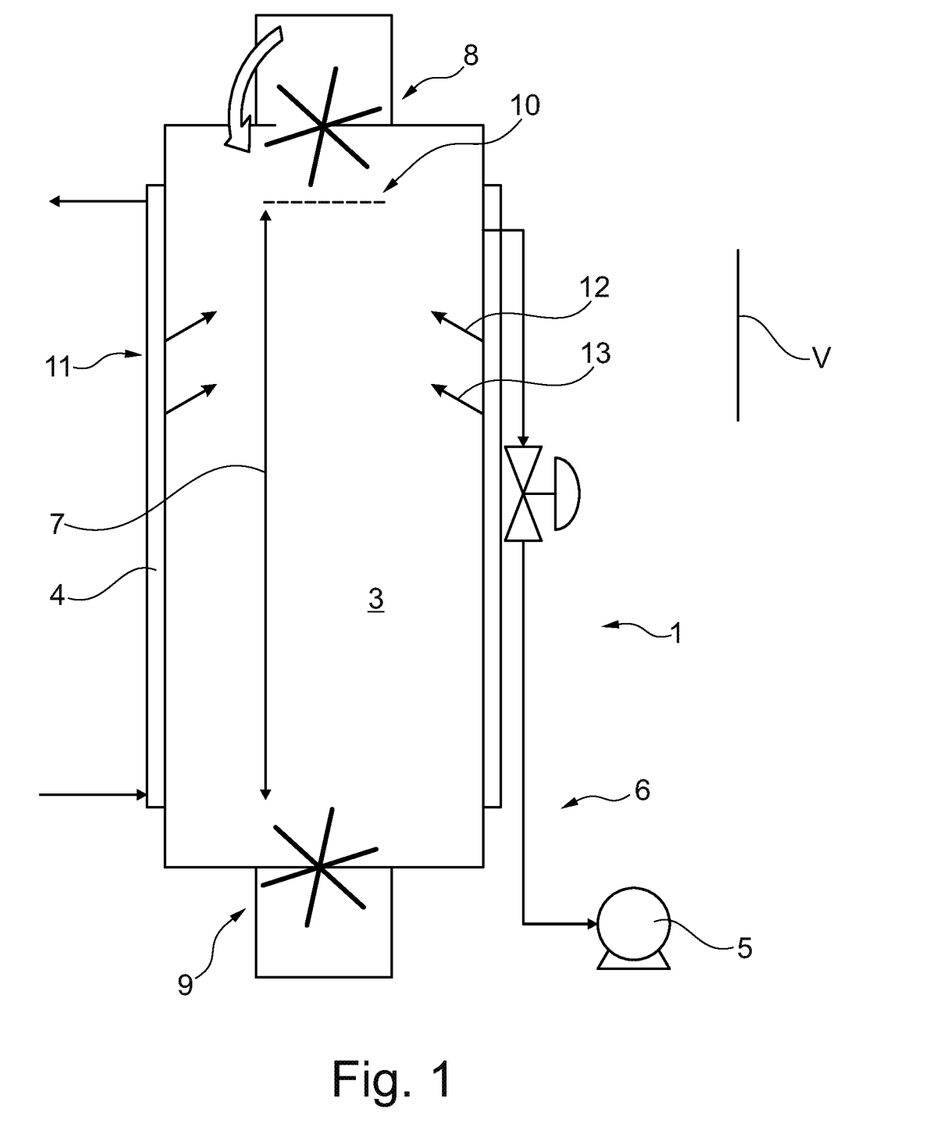
FIG. 1 is a highly schematized view of a sterilization device realized according to the idea of the invention for performing a method according to the invention.

In FIG. 1, a sterilization device 1 is shown. Sterilization device 1 comprises a vessel 2 which is made of stainless steel, for example, and which is elongated along the vertical and which limits an elongated treatment chamber 3 (reactor chamber). The realistic diameter length ratio cannot be derived from the schematic view—in fact, the diameter of treatment chamber 3 is considerably smaller than its length and height extension.

Vessel 2 or treatment chamber 3 can be heated, for example to a temperature of 300° C., via heating means 4 comprising a wall heating device, which is realized as an oil heating device in the present case. The arrows in the left drawing portion illustrate the flow and return flow. Treatment chamber 3 can be evacuated, i.e., can reach a negative pressure level, by means of evacuation means 6 comprising a vacuum pump 5.

Treatment chamber 3 comprises a drop section 7 which extends along vertical V and along which powder supplied via an inlet negative pressure lock 8, in an exemplary manner realized as an impeller lock, can fall freely downwards along vertical V inside evacuated treatment chamber 3 towards an outlet negative pressure lock 9 also realized as an impeller lock in an exemplary manner. Instead of an impeller lock, a preferably vacuum-based powder metering device is preferably used as inlet negative pressure lock 8 for metering powder portions to be sterilized one after the other.

In the shown exemplary embodiment, facultative dispersing means 10 are disposed downstream of inlet negative pressure lock 8 in order to improve powder cloud formation or loosening of the supplied powder. In the shown exemplary embodiment, dispersing means 10 comprise a vibrating grid.

Drop section 7 is divided into an upper fluid vapor application section in which fluid vapor can be applied to the free-falling powder, in particular in the form of a powder cloud. To this end, fluid vapor application means 11 (shown in a highly schematized and sectional manner) are provided. In the specific exemplary embodiment, said fluid vapor application means 11 comprise two ring nozzle assemblies 12, 13 which are spaced apart along vertical V and which are connected to a vapor generator via a corresponding vapor line for generating saturated vapor. A drying section is disposed below the fluid vapor application section, the powder to which the fluid vapor has been applied being dried or dryable in said drying section by the evaporation of the condensate formed on the powder surface by the fluid vapor application. This is achieved by a corresponding negative pressure atmosphere during the free fall through the drying section.

When the sterilized and dried powder reaches the lower area, it is discharged from treatment chamber 3, which is at a negative pressure level, via outlet negative pressure lock 9.

FIG. 1 shows that, in the present embodiment, the powder is supplied and treated in portions, in such a manner that a supplied powder portion to be sterilized is optionally loosened or dispersed by means of dispersing means 10 and then falls down along drop section 7 in evacuated treatment chamber 3 while fluid vapor, steam in the present case, is applied to the powder portion. The powder with the condensate which is condensed thereon continues to trickle down and is simultaneously dried. As will be explained on the basis of FIG. 2, the fluid vapor application causes the pressure level in vessel 2 to rise, starting from a first negative pressure level, to a second pressure level, for example to or even above a normal pressure (alternatively to a higher negative pressure level), evacuation means 6 ensuring that a sufficient negative pressure level is reached again at least during a period of time of the free fall along the drying section of the drop section in order to evaporate the condensate. A third negative pressure level is reached towards the end of the drying process at the latest.

Figure 2:
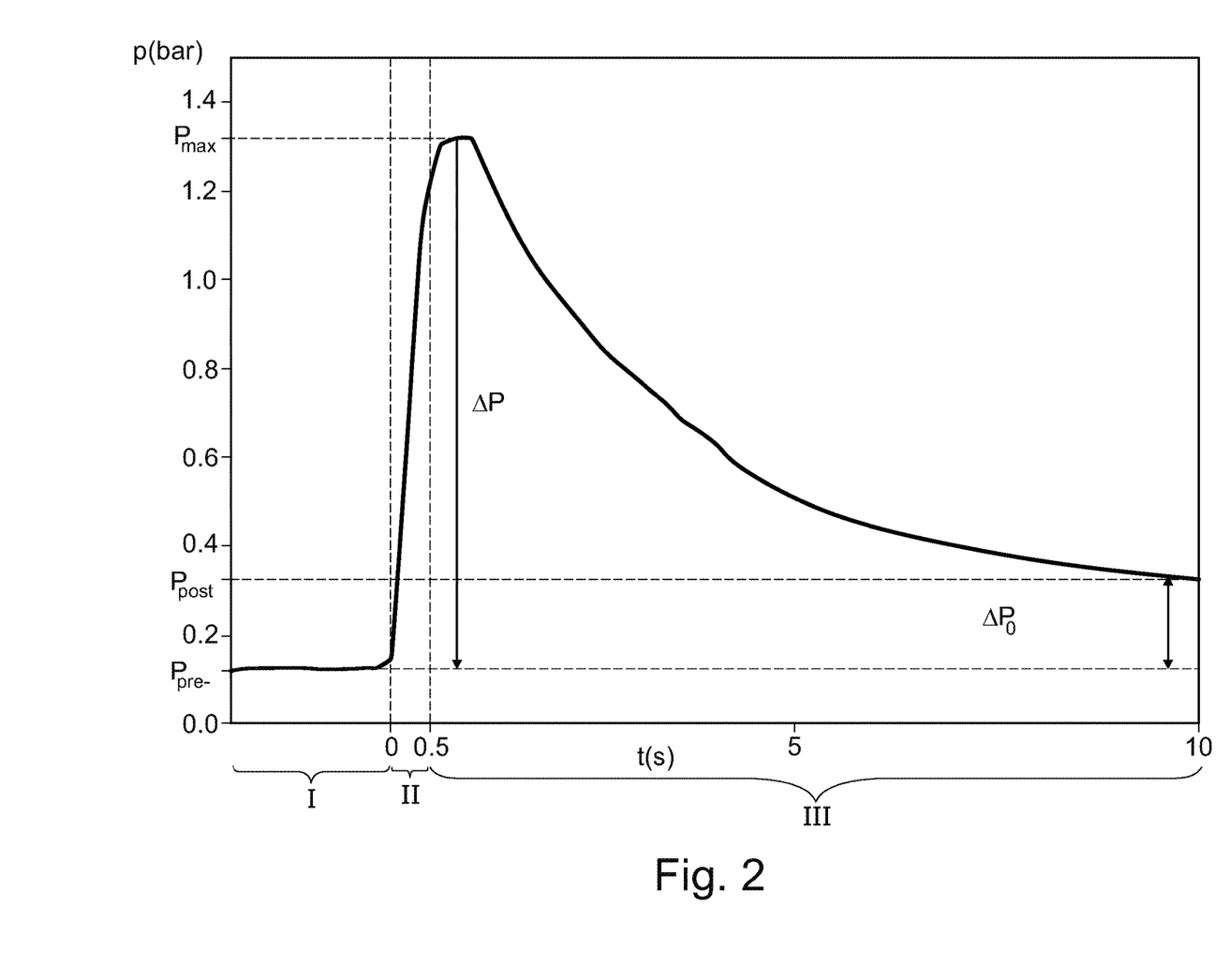
FIG. 2 is a diagram showing the absolute pressure in a treatment chamber of the sterilization device over time, i.e., during a sterilization and drying process.
Figure 3:
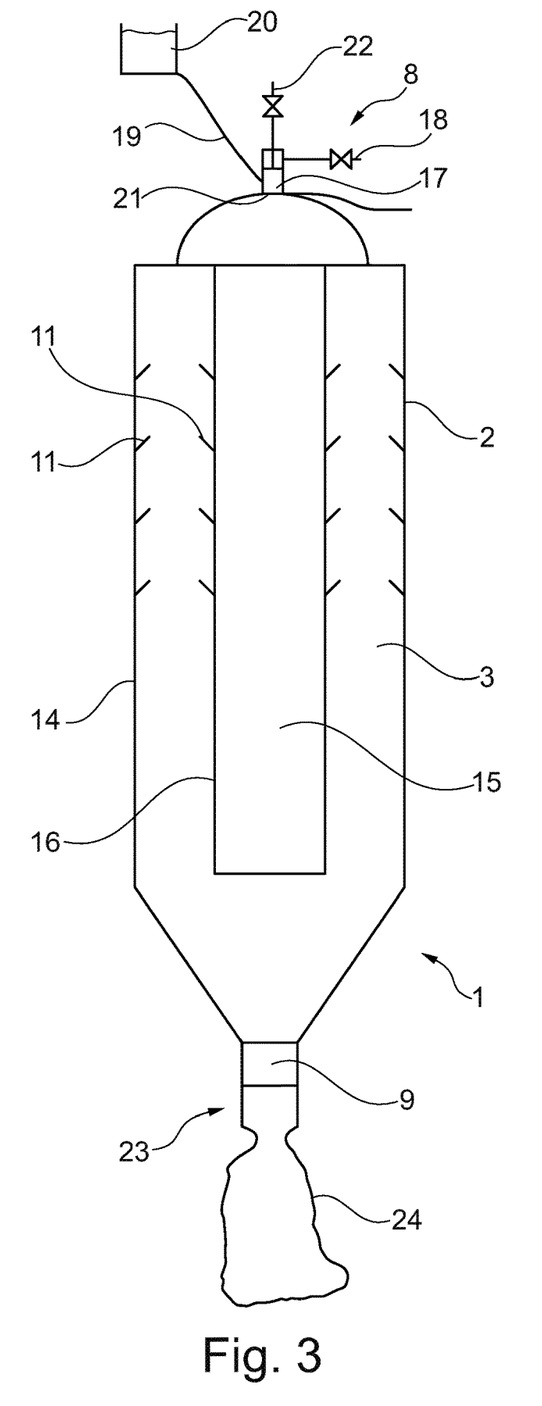
FIG. 3 is an alternative embodiment of a sterilization device realized according to the idea of the invention and comprising a treatment chamber which has an annular contour in a cross-sectional view and into which vapor for sterilizing the powder during the free fall can be supplied or is supplied from the radial inside and from the radial outside.
Figure 4:
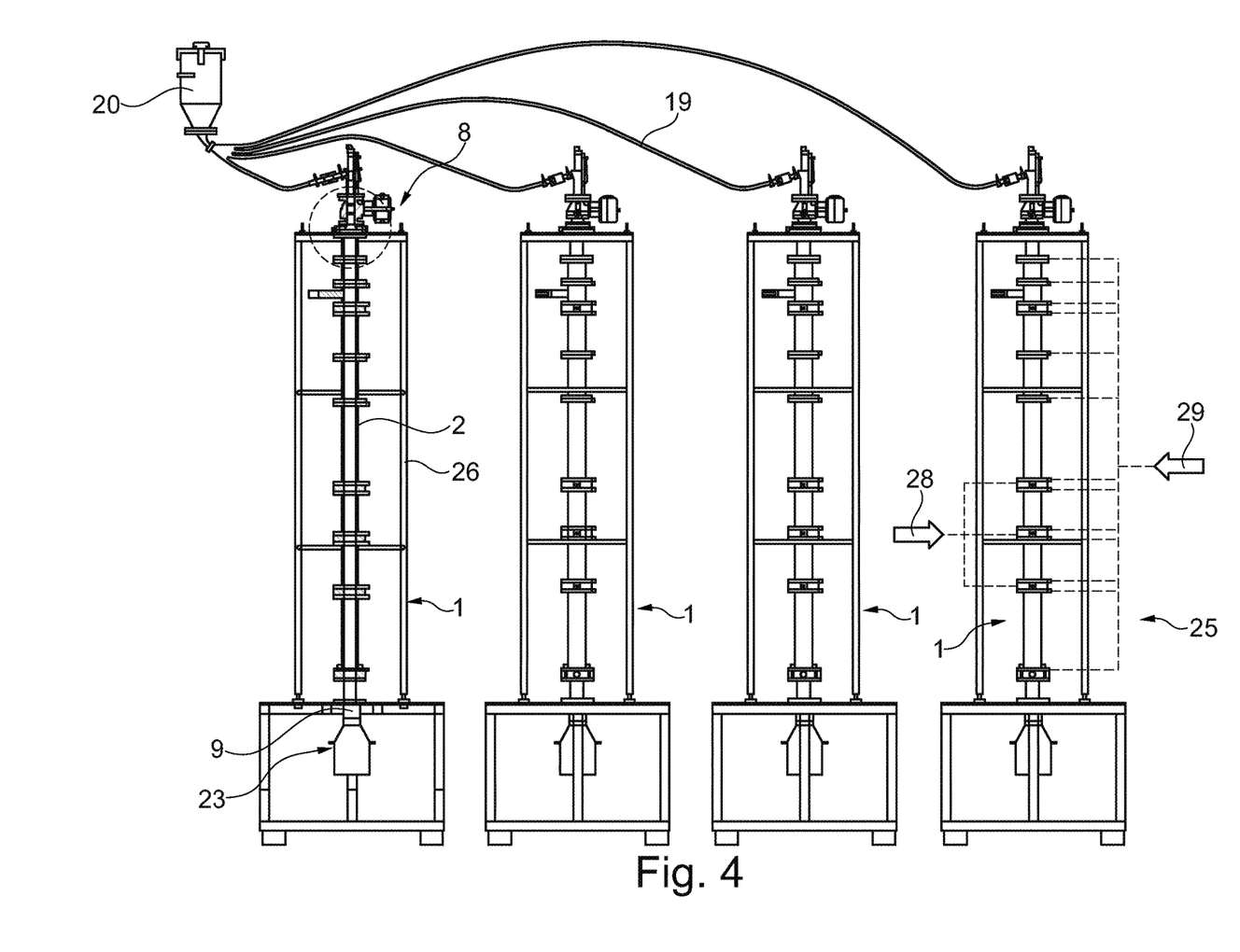
FIG. 4 is an alternative embodiment of a system which has four sterilization devices which are operated in parallel and to which powder to be sterilized can be supplied in portions and in a volume-metered manner via the negative pressure lock.
Figure 5A:
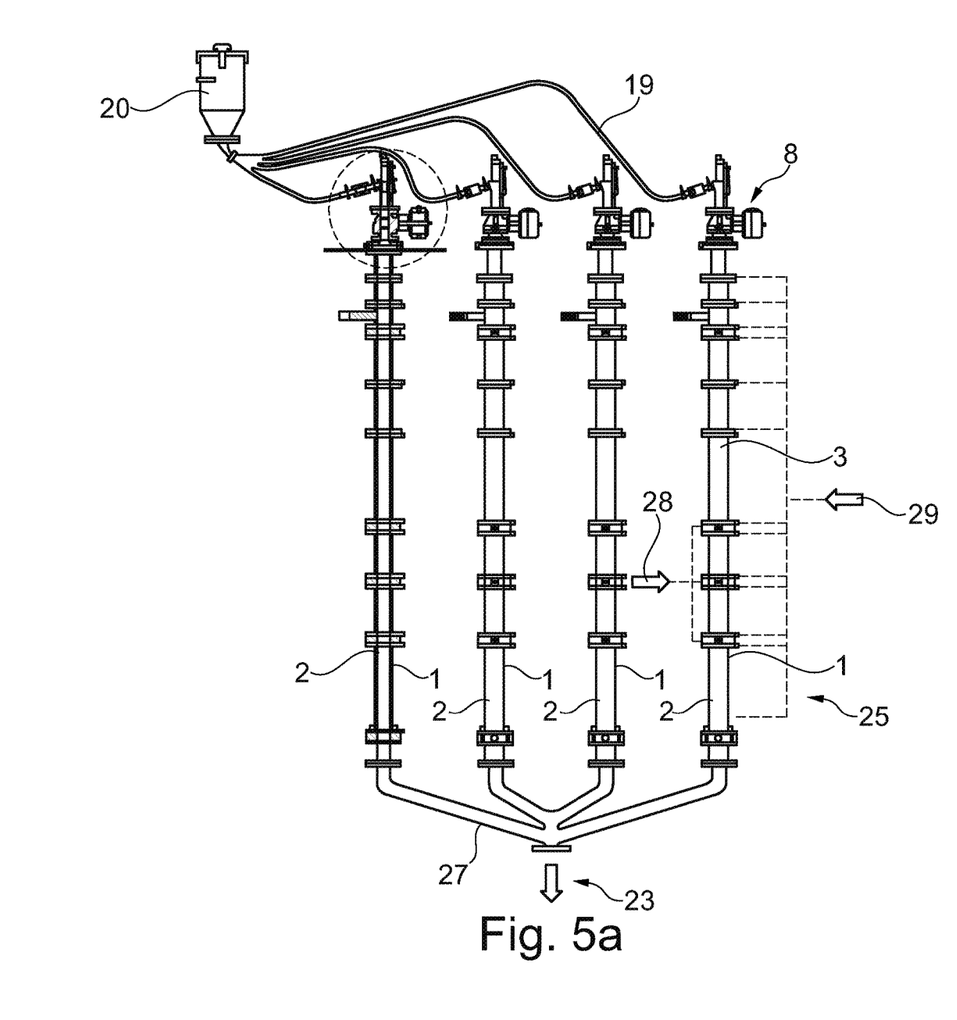
FIG. 5a is a system comprising four sterilization devices realized according to the idea of the invention which are connected to a common packaging device on the outlet side and into which, by analogy with the sterilization device according to FIG. 3 and FIG. 4, powder portions to be sterilized are not supplied via an impeller lock, but via volumetric volume metering devices based on negative pressure.
Figure 5B:
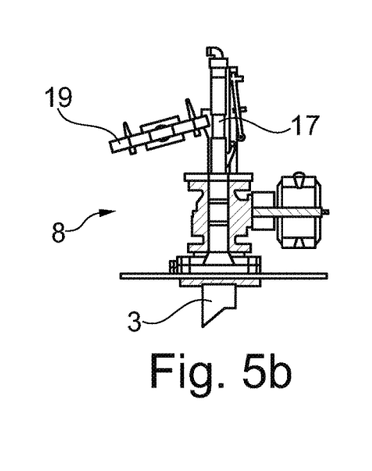
FIG. 5b is a vacuum-based volume metering device as a vacuum lock which is used in the system shown in FIG. 5a and FIG. 4.

In FIG. 2, a possible pressure development in the treatment chamber during a combined sterilization and drying process for a respective powder portion is shown, i.e., plotted over time. Said process repeats over time for each new powder portion which is supplied into treatment chamber 3.

It can be seen that a powder portion is supplied into the treatment chamber, is loosened, if required, and starts to fall along the drop section during a first period of time I during which a first negative pressure level at a pressure $P_{pre}$ of approximately 0.12 bar absolute is present in the present case. During the period of time II of 0.2 s in the present case, fluid vapor is applied to the powder during its free fall along the fluid vapor application section of the drop section, the pressure thus increasing to a second pressure level (in the present case a pressure $P_{max}$ of 1.3 bar absolute, for example). During the subsequent, longest period of time III, the powder falls along the longer drying section of the drop section, the pressure level being reduced during this continuing free fall, in the present case to a third negative pressure level ($P_{post}$), i.e., a pressure of approximately 0.35 bar absolute, which is slightly higher, namely by pressure difference $\Delta P_0$, than the initial, first pressure level $P_{pre}$. The dried powder is then discharged. Prior to a new supply of a next powder portion, the pressure level is preferably reduced from $P_{post}$ to $P_{pre}$. If the vacuum pump and the length of the drop section are dimensioned in a corresponding manner, a third negative pressure level ($P_{post}$) can preferably be reached during the free fall, said third negative pressure level being reduced to first pressure level $P_{pre}$.

Alternative exemplary embodiments realized according to the idea of the invention are explained below, differences compared to the aforementioned exemplary embodiments being primarily explained in order to avoid repetitions. Components of exemplary embodiments described below can be replaced by components of the aforementioned exemplary embodiments and vice versa.

In FIG. 3, a sterilization device 1 is shown in which treatment chamber 3 is annular, in the present case circular, in a cross-sectional view. Vessel 2 comprises a radially outer wall 14 which limits vessel 2 on the radial outside by analogy with the aforementioned exemplary embodiments. In a central area, vessel 2 comprises or includes a (in the present case circular-cylindrical) center section 15 which has an inner vessel wall 16 which limits treatment chamber 3 on the radial inside. It can be seen that fluid vapor application means 11, in an exemplary manner in the form of ring nozzle assemblies, are disposed on the radial outside, i.e., both in the area of outer wall 14 and on the radial inside, i.e., in the area of inner wall 16 of center section 15, in order to be able to supply fluid vapor both from the radial outside and from the radial inside, in particular diagonally upwards into treatment chamber 3 in order to ensure uniform mixing with the powder to be sterilized during the free fall. In the present case, center section 15 extends up to an upper edge of the vessel; alternatively, treatment chamber 3 can be free in its center area in an upper area.

In the present case, inlet negative pressure lock 8 is realized as a vacuum-operated volume metering device instead of an impeller lock. To this end, inlet negative pressure lock 8 comprises a metering chamber 17 to which negative pressure is applicable via a negative pressure line 18 in order to be able to suck powder from a powder reservoir 20 (powder reservoir vessel) via a supply line 19. Metering chamber 17 is closed on the outlet side via closing means 21. After filling metering chamber 17, in particular sterile compressed air is applied to metering chamber 17 via a compressed gas line 22 and metering chamber 17 is opened towards vessel 2 or treatment chamber 3 by displacing closing means 21 in a corresponding manner and the metered powder volume is supplied into treatment chamber 3 which, in an exemplary manner only, has an annular contour. To avoid confusion, facultative dispersing means are not illustrated. After falling through the drop section, the powder which has been sterilized by applying vapor and which has been dried during the free fall arrives at an outlet negative pressure lock 9 which leads to a packaging device 23 which is located directly downstream and by means of which the powder can be packed into final packaging 24, which is realized as pouches in the present case, by gravity.

The exemplary embodiment according to FIG. 4 is a system 25 having several sterilization devices 1. Respective elongated vessels 2 each having an integrated drop section 7 and nozzle assemblies for injecting vapor are shown. In a lower area, each sterilization device 1 has an individual packaging device 23.

Supports 26 which support respective vessels 2 and respective inlet negative pressure locks 8 can be seen, one inlet negative pressure lock 8 being shown in isolation on the right in the drawing layer. Inlet negative pressure lock 8, which is shown in principle in FIG. 3, is realized as a vacuum-based metering device by means of which powder can be sucked from a powder reservoir 20, which is a common powder reservoir 20 in the example at hand, via a supply line 19 and supplied in portions to the respective vessel in a volumetrically metered manner, preferably by applying negative pressure and/or by means of a discharge plunger, after opening the closing means of the metering chamber.

The exemplary embodiment according to FIGS. 5*a* and 5*b* essentially corresponds to the exemplary embodiment according to FIG. 4 but differs from the exemplary embodiment according to FIG. 4 in that individual sterilization devices 1 or their vessels 2 are connected to one another on the outlet side via pipelines 27 leading to a common packaging device 23 or, alternatively, to a common reservoir. In the exemplary embodiment according to FIG. 5*a*, the inlet negative pressure locks are also realized as volume metering devices which suck powder from a powder reservoir 20 via supply lines 19 and which supply said powder to respective treatment chamber 3 by means of a plunger and/or by applying compressed gas after opening metering chamber closing means.

Reference sign 28 shows preferably superheated vapor being supplied into a vapor distribution system by means of which vapor can be supplied to the outlet openings, in particular the ring nozzle assemblies, which are disposed in treatment chamber 3. Reference sign 29 is assigned to a heating means flow, in the present case an oil flow for the heating of the outer wall.

REFERENCE SIGNS

1 sterilization device
2 vessel
3 treatment chamber
4 heating means
5 vacuum pump
6 evacuation means
7 drop section
8 inlet negative pressure lock
9 outlet negative pressure lock
10 dispersing means
11 fluid vapor application means
12 ring nozzle assembly
13 ring nozzle assembly
14 outer vessel wall
15 center section
16 inner vessel wall
17 metering chamber
18 negative pressure line
19 supply line
20 powder reservoir 21 closing means
22 compressed air line
23 packaging device
24 final packaging
25 system
26 support
27 pipelines
28 arrow (vapor supply)
29 arrow (heating means flow)
V vertical
$P_{pre}$ negative pressure level while powder is being supplied (first negative pressure level
$P_{max}$ pressure level immediately after fluid vapor application (second negative pressure level)
$P_{post}$ negative pressure level at the end of the drying process (third negative pressure level)

The invention claimed is:

1. A powder sterilization method for sterilizing powder using fluid vapor,
the fluid vapor being applied to the powder in an evacuated treatment chamber (3),
the fluid vapor being applied to the powder during a free fall of the powder along a drop section (7),
wherein evacuation means for providing a negative pressure in the treatment chamber (3) are operated in a permanent and continuous manner to provide a negative pressure in the treatment chamber,
a suction pressure thus being permanently applied and the application of the fluid vapor causing the pressure to rise during the free fall after the powder has been supplied, and
the evacuation means continuing to apply suction to the treatment chamber (3) during said fluid vapor application.

2. The method according to claim 1, wherein the fluid vapor condenses on a powder surface and the powder is dried by evaporating condensate from the powder surface, during the free fall, before discharging the powder from the treatment chamber (3).

3. The method according to claim 1 wherein the powder to be sterilized is supplied to the treatment chamber (3) when the treatment chamber (3) is at a first negative pressure level (Ppre), between 0.1 mbar and 300 mbar, and the fluid vapor is applied to said powder during the free fall along the drop section (7), and wherein the pressure in the treatment chamber (3) rises to a second pressure level (Pmax) above 0.5 bar, and wherein the pressure level is reduced for drying the powder before the powder is discharged from the treatment chamber (3), while the powder is still falling freely along the drop section (7), to a third negative pressure value (Ppost).

4. The method according to claim 1, wherein powder to be sterilized is supplied to the treatment chamber (3) via an inlet negative pressure lock (8), and wherein sterilized powder is discharged from the treatment chamber (3) via an outlet negative pressure lock (9), after the free fall along the drop section (7) and after the application of fluid vapor carried out during the free fall.

5. The method according to claim 4, wherein powder to be sterilized is supplied to the treatment chamber (3) solely during, or solely after, or during and after the discharging of sterilized powder.

6. The method according to claim 1, wherein the fluid vapor enters the treatment chamber (3) at an increased pressure compared to the pressure level in the treatment chamber (3) at the time the fluid vapor application starts.

7. The method according to claim 1, wherein the fluid vapor enters the treatment chamber (3) at an angle between a main jetting direction of the fluid vapor and vertical (V) between 1° and 60°.

8. The method according to claim 1, wherein the fluid vapor enters the treatment chamber (3) at several points spaced apart along the drop section (7) and/or at several points spaced apart in the circumferential direction.

9. The method according to claim 1, wherein the fluid vapor enters the treatment chamber (3) via at least one ring nozzle assembly (12, 13) extending in the circumferential direction along the drop section (7).

10. The method according to claim 1, wherein the fluid vapor is saturated or superheated when it enters the treatment chamber (3).

11. The method according to claim 1, wherein the treatment chamber (3) is heated to a temperature from a range between 150° C. and 400° C. by means of a wall heating device.

12. The method according to claim 1, wherein the powder is dispersed and/or separated and/or swirled and/or loosened, above and/or in an initial area of the drop section (7), in order to improve powder cloud formation.

* * * * *